US009610285B2

(12) United States Patent
Avena et al.

(10) Patent No.: US 9,610,285 B2
(45) Date of Patent: Apr. 4, 2017

(54) COMPOSITIONS FOR CONTROLLING FOOD INTAKE AND USES THEREFOR

(71) Applicant: UNIVERSITY OF FLORIDA RESEARCH FOUNDATION, INCORPORATED, Gainesville, FL (US)

(72) Inventors: Nicole M. Avena, Clarksburg, NJ (US); Mark S. Gold, Alachua, FL (US)

(73) Assignee: UNIVERSITY OF FLORIDA RESEARCH FOUNDATION, INCORPORATED, Gainesville, FL (US)

( * ) Notice: Subject to any disclaimer, the term of this patent is extended or adjusted under 35 U.S.C. 154(b) by 134 days.

(21) Appl. No.: 14/358,418

(22) PCT Filed: Nov. 16, 2012

(86) PCT No.: PCT/US2012/065486
§ 371 (c)(1),
(2) Date: May 15, 2014

(87) PCT Pub. No.: WO2013/074906
PCT Pub. Date: May 23, 2013

(65) Prior Publication Data
US 2014/0315938 A1 Oct. 23, 2014

Related U.S. Application Data

(60) Provisional application No. 61/560,356, filed on Nov. 16, 2011.

(51) Int. Cl.
*A61K 31/485* (2006.01)
*A61K 31/197* (2006.01)
*A61K 31/137* (2006.01)
*A61K 45/06* (2006.01)
*A61K 31/16* (2006.01)

(52) U.S. Cl.
CPC .......... *A61K 31/485* (2013.01); *A61K 31/137* (2013.01); *A61K 31/16* (2013.01); *A61K 31/197* (2013.01); *A61K 45/06* (2013.01); *Y10S 514/909* (2013.01)

(58) Field of Classification Search
None
See application file for complete search history.

(56) References Cited

U.S. PATENT DOCUMENTS

| | | | |
|---|---|---|---|
| 2002/0044968 A1 | 4/2002 | van Lengerich | |
| 2007/0072899 A1 | 3/2007 | Johnson et al. | |
| 2007/0099947 A1* | 5/2007 | Dean, III | A61K 31/4745 |
| 2007/0129283 A1 | 6/2007 | McKinney et al. | |
| 2008/0293777 A1 | 11/2008 | Erlanson et al. | |

OTHER PUBLICATIONS

Colombo et al., Drug and Alcohol Dependence, 2005, vol. 77, pp. 87-91.*
Stromberg, "The effect of baclofen alone and in combination with naltrexone on ethanol consumption in the rat", Pharmacology, Biochemistry and Behavior, 2004, vol. 78, pp. 743-750.*
Williams, "Medications for Treating Alcohol Dependence", American Family Physician, 2005, vol. 72(9), pp. 1775-1780.*
Greenway et al., "Effect of naltrexone plus bupropion on weight loss in overweight and obese adults (COR-I): a multicentre, randomised, double-blind, placebo-controlled, phase 3 trial", Lancet, published online Oct. 2010, vol. 376, pp. 595-605.*
Addolorato, G. et al. "Baclofen Efficacy in Reducing Alcohol Craving and Intake: A Preliminary Double-Blind Randomized Controlled Study," Alcohol & Alcoholism, 2002, pp. 504-508, vol. 37, No. 5.
Alger, S. A. et al. "Effect of a tricyclic antidepressant and opiate antagonist on binge-eating behavior in normoweight bulimic and obese, binge-eating subjects," Am J Clin Nutr, 1991, pp. 865-871, vol. 53.
Arima, H. et al. "Positive Effect of Baclofen on Body Weight Reduction in Obese Subjects: A Pilot Study," Inter Med, 2010, pp. 2043-2047, vol. 49.
Buda-Levin, A. et al. "Baclofen reduces fat intake under binge-type conditions," Physiology & Behavior, 2005, pp. 176-184, vol. 86.
Colombo, G. et al. "Effect of the combination of naltrexone and baclofen, on acquisition of alcohol drinking behavior in alcohol-preferring rats," Drug and Alcohol Dependence, 2005, pp. 87-91, vol. 77.
Dym, C. T. et al. "Genetic Variance Contributes to Dopamine and Opioid Receptor Antagonist-Induced Inhibition of Intralipid (Fat) Intake in Inbred and Outbred Mouse Strains," Brain Res., Feb. 26, 2010, pp. 1-17.
Greenway, F. L. et al. "Rational design of a combination medication for the treatment of obesity," Obesity (Silver Spring), Jan. 2009, pp. 30-39, vol. 17, No. 1, Abstract only.
Kiefer, F. et al. "Comparing and Combining Naltrexone and Acamprosate in Relapse Prevention of Alcoholism," Arch Gen Psychiatry, 2003, pp. 92-99, vol. 60.
"Orexigen(R) Therapeutics and Takeda Enter Into Partnership to Commercialize Contrave(R) in North America," Orexigen Therapeutics Inc.—Investor Relations—Press Release, pp. 1-3. Sep. 2, 2010.
Liu, Y. et al. "Food Addiction and Obesity: Evidence from Bench to Bedside" Journal of Psychoactive Drugs, Jun. 2010, pp. 135-145, vol. 42, No. 2.
Written Opinion in International Application No. PCT/US2012/065486, Feb. 28, 2013, pp. 1-7.

* cited by examiner

Primary Examiner — Savitha Rao
Assistant Examiner — Gregg Polansky
(74) Attorney, Agent, or Firm — Saliwanchik, Lloyd & Eisenschenk

(57) ABSTRACT

The present invention is directed to a combination treatment for: individuals who meet the definition of food addiction; individuals who are overweight or obese (e.g., a BMI≥25); individuals who have a binge eating disorder; or individuals who engage in a binge eating behavior. In particular embodiments, the combination therapy reduces the intake of fatty foods, sugar-rich foods, or foods that are both fatty and sugar-rich (e.g., fast foods).

7 Claims, 8 Drawing Sheets

Yale Food Addiction Scale

Gearhardt, Corbin, Brownell, 2009
Contact: ashley.gearhardt@yale.edu

This survey asks about your eating habits in the past year. People sometimes have difficulty controlling their intake of certain foods such as:
- Sweets like ice cream, chocolate, doughnuts, cookies, cake, candy, ice cream
- Starches like white bread, rolls, pasta, and rice
- Salty snacks like chips, pretzels, and crackers
- Fatty foods like steak, bacon, hamburgers, cheeseburgers, pizza, and French fries
- Sugary drinks like soda pop When the following questions ask about "CERTAIN FOODS" please think of ANY food similar to those listed in the food group or ANY OTHER foods you have had a problem with in the past year

| IN THE PAST 12 MONTHS: | Never | Once a month | 2-4 times a month | 2-3 times a week | 4 or more times or daily |
|---|---|---|---|---|---|
| 1. I find that when I start eating certain foods, I end up eating much more than planned | 0 | 1 | 2 | 3 | 4 |
| 2. I find myself continuing to consume certain foods even though I am no longer hungry | 0 | 1 | 2 | 3 | 4 |
| 3. I eat to the point where I feel physically ill | 0 | 1 | 2 | 3 | 4 |
| 4. Not eating certain types of food or cutting down on certain types of food is something I worry about | 0 | 1 | 2 | 3 | 4 |
| 5. I spend a lot of time feeling sluggish or fatigued from overeating | 0 | 1 | 2 | 3 | 4 |
| 6. I find myself constantly eating certain foods throughout the day | 0 | 1 | 2 | 3 | 4 |
| 7. I find that when certain foods are not available, I will go out of my way to obtain them. For example, I will drive to the store to purchase certain foods even though I have other options available to me at home. | 0 | 1 | 2 | 3 | 4 |
| 8. There have been times when I consumed certain foods so often or in such large quantities that I started to eat food instead of working, spending time with my family or friends, or engaging in other important activities or recreational activities I enjoy. | 0 | 1 | 2 | 3 | 4 |
| 9. There have been times when I consumed certain foods so often or in such large quantities that I spent time dealing with negative feelings from overeating instead of working, spending time with my family or friends, or engaging in other important activities or recreational activities I enjoy. | 0 | 1 | 2 | 3 | 4 |
| 10. There have been times when I avoided professional or social situations where certain foods were available, because I was afraid I would overeat. | 0 | 1 | 2 | 3 | 4 |
| 11. There have been times when I avoided professional or social situations because I was not able to consume certain foods there. | 0 | 1 | 2 | 3 | 4 |
| 12. I have had withdrawal symptoms such as agitation, anxiety, or other physical symptoms when I cut down or stopped eating certain foods. (Please do NOT include withdrawal symptoms caused by cutting down on caffeinated beverages such as soda pop, coffee, tea, energy drinks, etc.) | 0 | 1 | 2 | 3 | 4 |
| 13. I have consumed certain foods to prevent feelings of anxiety, agitation, or other physical symptoms that were developing. (Please do NOT include consumption of caffeinated beverages such as soda pop, coffee, tea, energy drinks, etc.) | 0 | 1 | 2 | 3 | 4 |
| 14. I have found that I have elevated desire for or urges to consume certain foods when I cut down or stop eating them. | 0 | 1 | 2 | 3 | 4 |
| 15. My behavior with respect to food and eating causes significant distress. | 0 | 1 | 2 | 3 | 4 |
| 16. I experience significant problems in my ability to function effectively (daily routine, job/school, social activities, family activities, health difficulties) because of food and eating. | 0 | 1 | 2 | 3 | 4 |

FIG. 6

| IN THE PAST 12 MONTHS: | NO | YES |
|---|---|---|
| 17. My food consumption has caused significant psychological problems such as depression, anxiety, self-loathing, or guilt. | 0 | 1 |
| 18. My food consumption has caused significant physical problems or made a physical problem worse. | 0 | 1 |
| 19. I kept consuming the same types of food or the same amount of food even though I was having emotional and/or physical problems. | 0 | 1 |
| 20. Over time, I have found that I need to eat more and more to get the feeling I want, such as reduced negative emotions or increased pleasure. | 0 | 1 |
| 21. I have found that eating the same amount of food does not reduce my negative emotions or increase pleasurable feelings the way it used to. | 0 | 1 |
| 22. I want to cut down or stop eating certain kinds of food. | 0 | 1 |
| 23. I have tried to cut down or stop eating certain kinds of food. | 0 | 1 |
| 24. I have been successful at cutting down or not eating these kinds of food | 0 | 1 |

25. How many times in the past year did you try to cut down or stop eating certain foods altogether?

| 1 time | 2 times | 3 times | 4 times | 5 or more times |
|---|---|---|---|---|
| | | | | |

26. Please circle ALL of the following foods you have problems with:

| Ice cream | Chocolate | Apples | Doughnuts | Broccoli | Cookies | Cake | Candy |
|---|---|---|---|---|---|---|---|
| White Bread | Rolls | Lettuce | Pasta | Strawberries | Rice | Crackers | Chips |
| Pretzels | French Fries | Carrots | Steak | Bananas | Bacon | Hamburgers | Cheese burgers |
| Pizza | Soda Pop | None of the above | | | | | |

27. Please list any other foods that you have problems with that were not previously listed:

FIG. 6 (continued)

COMPOSITIONS FOR CONTROLLING FOOD INTAKE AND USES THEREFOR

CROSS-REFERENCE TO RELATED APPLICATIONS

This application is the U.S. national stage application of International Patent Application No. PCT/US2012/065486, filed Nov. 16, 2012, which claims the benefit of U.S. Provisional Patent Application Ser. No. 61/560,356, filed Nov. 16, 2011, the disclosures of which are hereby incorporated by reference in their entirety, including all figures, tables and nucleic acid sequences.

TECHNICAL FIELD

The present invention relates to a combination therapy for the treatment of food addiction, obesity, binge eating disorder, or binge eating behavior.

BRIEF SUMMARY OF THE INVENTION

The present invention is directed to a combination treatment of a mu-opioid receptor antagonist and a GABA B receptor agonist and, optionally, a third therapeutic agent selected from CB-1 receptor antagonists, glycine reuptake inhibitors, dopamine augmenting compounds, nicotine receptor agonists, psychostimulants, mGlu2/3 agonists, mGlu5 antagonists, glycine-site partial agonists, cystine-glutamate exchangers, cystine-glutamate activators, glutamate transporter inhibitors, mGlu5 receptor agonists or NMDA receptor co-agonists, for the treatment of individuals who meet the definition of food addiction; individuals who are overweight or obese (e.g., a BMI≥25); individuals who have a binge eating disorder; or individuals who engage in a binge eating behavior. Specific combinations of these classes of compounds are provided in Table 1. Tables 2-3 provide exemplary combinations of specific compounds suitable for the treatment of individuals who meet the definition of food addiction; individuals who are overweight or obese (e.g., a BMI≥25 or having a BMI between 25 and 35); individuals who have a binge eating disorder; or individuals who engage in a binge eating behavior. The invention may also be used for individuals who have difficulty in controlling the amounts of fast food consumed during a given period of time.

BRIEF DESCRIPTION OF THE DRAWINGS

FIG. 6. The Yale Food Addiction Scale (survey).

DETAILED DISCLOSURE OF THE INVENTION

Figure 1:
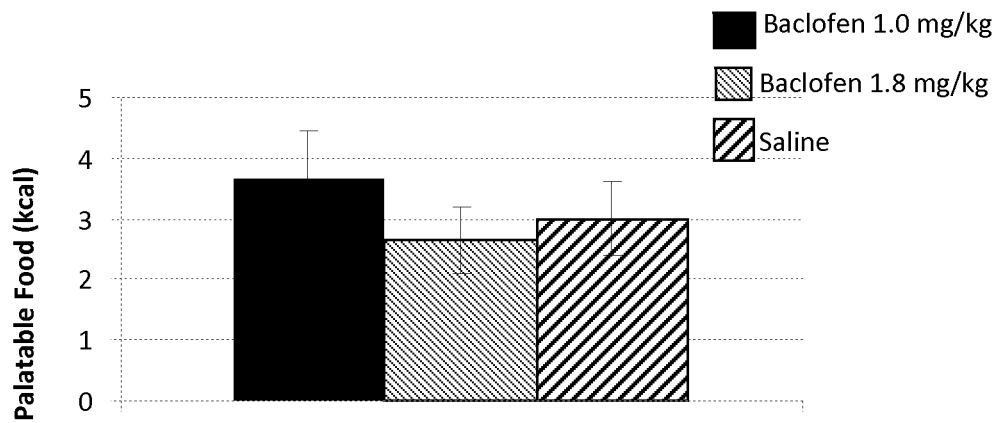
FIG. 1—Baclofen (alone) has no effect on binge eating of sugar.

The present invention is directed to a combination treatment of a mu-opioid receptor antagonist and a GABA B agonist and, optionally, a third therapeutic agent selected from CB-1 receptor antagonists, glycine reuptake inhibitors, dopamine augmenting compounds, nicotine receptor agonists, psychostimulants, mGlu2/3 agonists, mGlu5 antagonists, glycine-site partial agonists, cystine-glutamate exchangers, cystine-glutamate activators, glutamate transporter inhibitors, mGlu5 receptor agonists or NMDA receptor co-agonists, for the treatment of individuals who meet the definition of food addiction; individuals who are overweight or obese (e.g., a BMI≥25); individuals who have a binge eating disorder; or individuals who engage in a binge eating behavior. Specific combinations of these classes of compounds are provided in Table 1. Tables 2-3 provide exemplary combinations of specific compounds suitable for the treatment of individuals who meet the definition of food addiction; individuals who are overweight or obese (e.g., a BMI≥25 or having a BMI between 25 and 35); individuals who have a binge eating disorder; or individuals who engage in a binge eating behavior. The invention may also be used for individuals who have difficulty in controlling the amounts of fast food consumed during a given period of time.

The term "combination" as in the phrase "a first compound in combination with a second compound" includes co-administration of a first therapeutically effective compound and a second therapeutically effective compound, which for example may be dissolved or intermixed in the same pharmaceutically acceptable carrier. The term "concurrently administered" when referring to the various compounds disclosed herein indicates that the compounds can be administered separately at the same time or sequentially in any order at different points in time. The compounds, however, should be administered close in time so as to provide an effect suitable for the treatment of individuals who meet the definition of food addiction; individuals who are overweight or obese (e.g., a BMI≥25); individuals who have a binge eating disorder; or individuals who engage in a binge eating behavior. Typically, concurrently administered compounds are administered within 60 minutes of one another.

The term "synergistic effect" as used herein refers to the combined effect of administering two (or three) therapeutic compounds where the overall response is greater than the sum of the two individual effects (e.g., the effects observed when each compound is administered alone as a monotherapy).

The dosage of the individual therapeutic compounds that are to be administered to individuals may be adjusted to provide the optimal therapeutic response. Thus, the specific dose level for any particular patient may vary depending upon a variety of factors, including, but not limited to, the activity of the specific compound employed; the age, body weight, general health, sex and diet of the patient; the time of administration; the rate of excretion; the drug combination; the severity of the particular disease being treated; and the form of administration. Typically, in vitro dosage-effect results provide useful guidance on the proper doses for patient administration. The considerations for determining the proper dose levels are well-known in the art.

In one embodiment, naltrexone is co-administered or administered in combination with baclofen and, optionally, additional therapeutic compounds. In certain cases, naltrexone, in an amount of about 25 to 100 milligrams per day, and baclofen, in an amount ranging between about 15 and about 120 milligrams per day (preferably between about 20 milligrams and about 80 milligrams per day) can be administered in combination or co-administered. As set forth in the Tables, a combination of three therapeutic compounds can be used in the disclosed methods. For example, a combination of naltrexone, baclofen and acamprosate or bupropion (or bupropion extended release) can be co-administered or administered in combination to a subject according to the disclosed methods. In such embodiments, naltrexone, in an amount of about 25 to 100 milligrams per day, baclofen, in an amount ranging between about 15 and about 120 milligrams per day (preferably between about 20 milligrams and about 80 milligrams per day), and acamprosate, in an amount between about 300 and 2500 milligrams per day (e.g., as two 333-mg tablets taken three times a day), can be co-administered or administered in combination. Alternatively, naltrexone, in an amount of about 25 to 100 milligrams per day, baclofen, in an amount ranging between about 15 and about 120 milligrams per day (preferably between about 20 milligrams and about 80 milligrams per day), and bupropion (or bupropion extended release), in an amount of between 75 milligrams and 450 milligrams per day (preferably between about 150 and about 300 milligrams per day), can be co-administered or administered in combination within the disclosed methods. Other combinations of therapeutic compounds and compositions according to the invention are set forth in Tables 2 and 3.

The therapeutic compounds used in the disclosed combination therapies can be administered in oral forms. These include, but are not limited to, tablets, capsules, pills, powders, granules, elixirs, tinctures, suspensions, syrups, and emulsions. Rapid-release and time-controlled release (extended release) formulations of the disclosed therapeutic compounds can be used for the treatment of individuals who meet the definition of food addiction; individuals who are overweight or obese (e.g., a BMI≥25); individuals who have a binge eating disorder; or individuals who engage in a binge eating behavior. The therapeutic compounds disclosed herein can, typically, be administered in "pharmaceutically acceptable carriers" such as pharmaceutical diluents, pharmaceutical excipients or pharmaceutical carriers. For instance, tablets or capsules can comprise one or more of the disclosed therapeutic compounds and lactose, starch, sucrose, glucose, modified sugars, modified starches, methyl cellulose and its derivatives, dicalcium phosphate, calcium sulfate, mannitol, sorbitol and other reducing and non-reducing sugars, magnesium stearate, steric acid, sodium stearyl fumarate, glyceryl behenate, calcium stearate and the like. Liquid formulations can comprise one or more therapeutic agents in combination with ethanol, glycerol, water and the like. Additionally, the compositions can contain binders, lubricants, disintegrating agents, coloring agents and/or flavoring agents as desired.

In the context of the present invention, the term "individual" refers to a mammal. In particular embodiments, the mammal can be a rodent, such as a mouse or rat. In other embodiments, the mammal is a human. Individuals to whom the methods disclosed herein can be applied can be identified by a variety of means, including the use of body mass index (BMI) or surveys that identify individuals exhibiting symptoms of food addiction (e.g., the Yale Food Addiction Scale (see FIG. 6)).

Thus, certain aspects of the disclosed invention provide methods for the treatment of individuals who meet the definition of food addiction; individuals who are overweight or obese (e.g., a BMI≥25); individuals who have a binge eating disorder; or individuals who engage in a binge eating behavior. These methods comprise the administration of a composition as set forth in any one of Tables 1-3 to an individual meeting the definition of food addiction, an individual who is obese or overweight, an individual who has a binge-eating disorder or an individual who engages in binge eating behavior in amounts effective to control or reduce the intake of food. In preferred embodiments of this aspect of the invention, the foods are fatty foods, sugar-rich foods, or foods that are both fatty and sugar-rich.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) of any other invention or embodiment thereof disclosed herein, and all such combinations are contemplated within the scope of the invention without limitation thereto.

EXAMPLES

Example 1

Figure 2A:
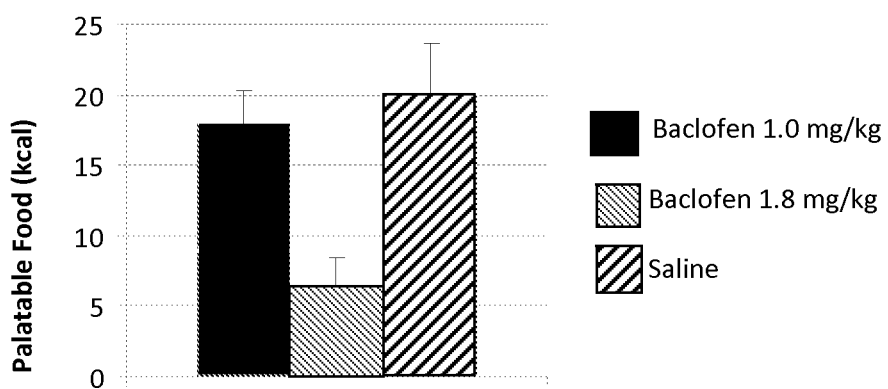
FIGS. 2A-2B—Baclofen (alone) reduces intake of oil-containing palatable foods.
Figure 2B:
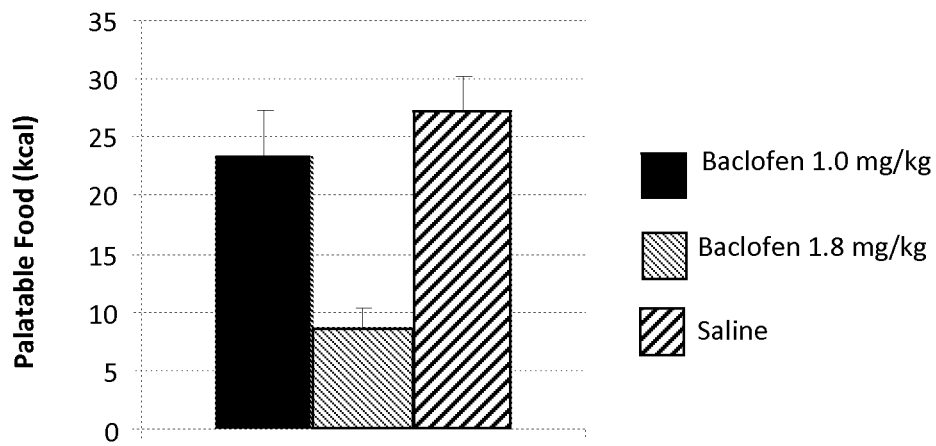
Figure 3A:
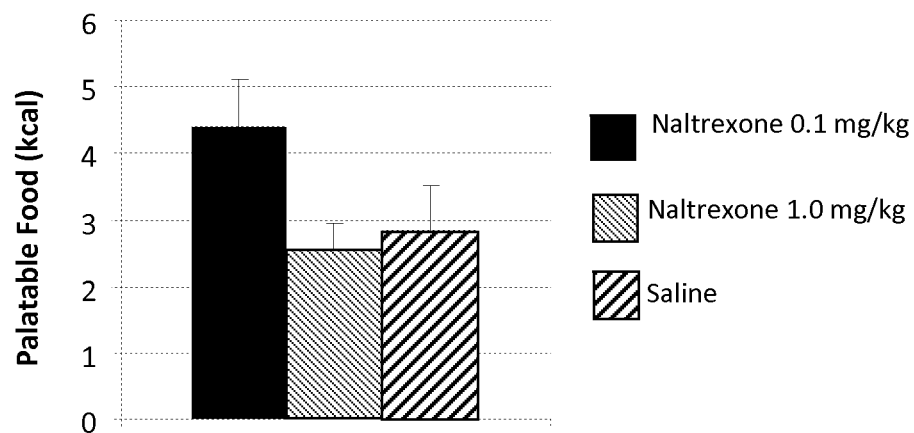
FIGS. 3A-3C—Naltrexone has a trend toward reducing food intake in the oil containing groups, but has no effect on sugar-binging rats.
Figure 3B:
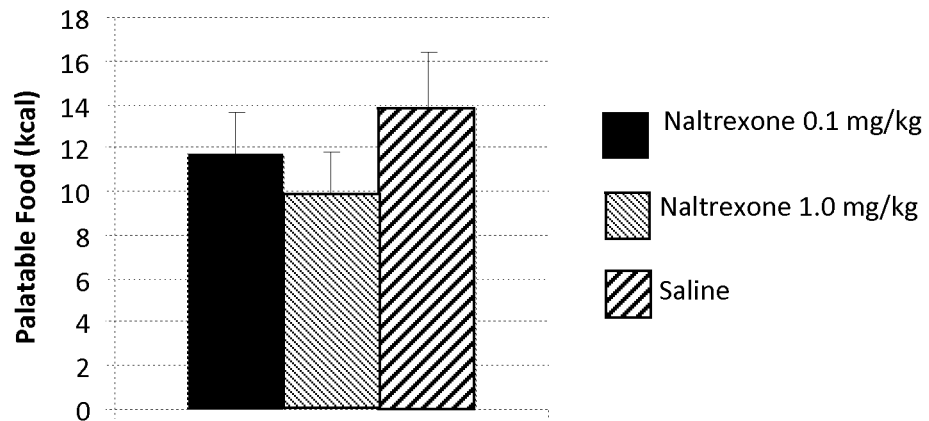
Figure 3C:
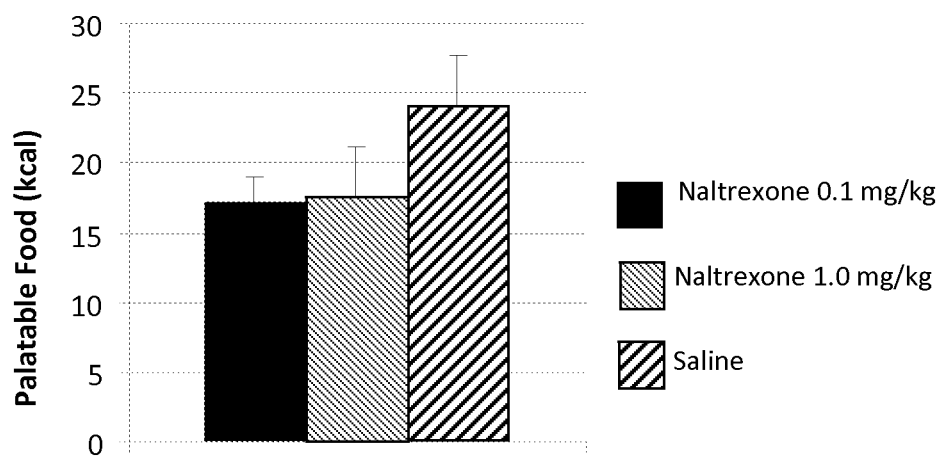
Figure 4A:
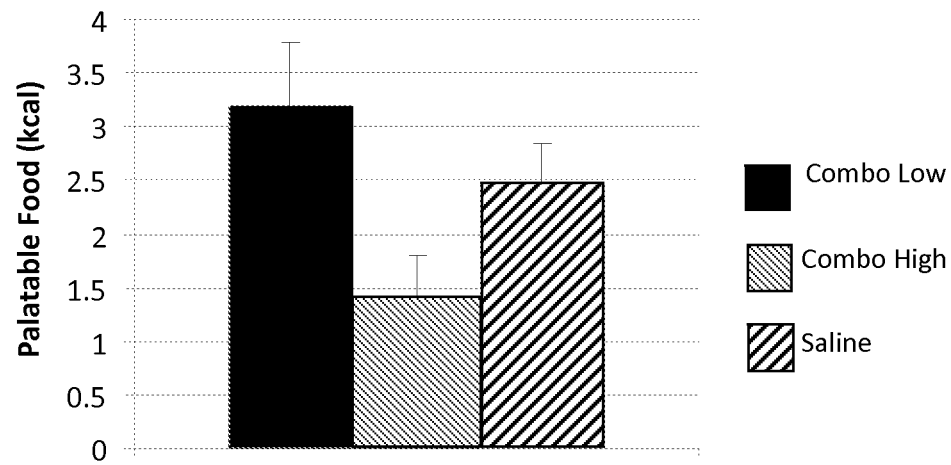
FIGS. 4A-4C. The combination of baclofen/naltrexone at higher doses (naltrexone at 1.0 mg/kg and baclofen at 1.8 mg/kg) robustly reduces intake of sugar, fat, or both fat and sugar.
Figure 4B:
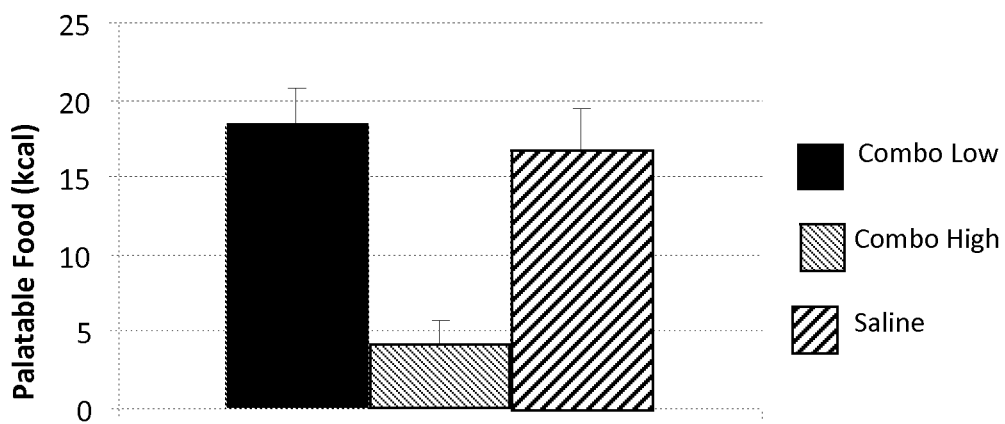
Figure 4C:
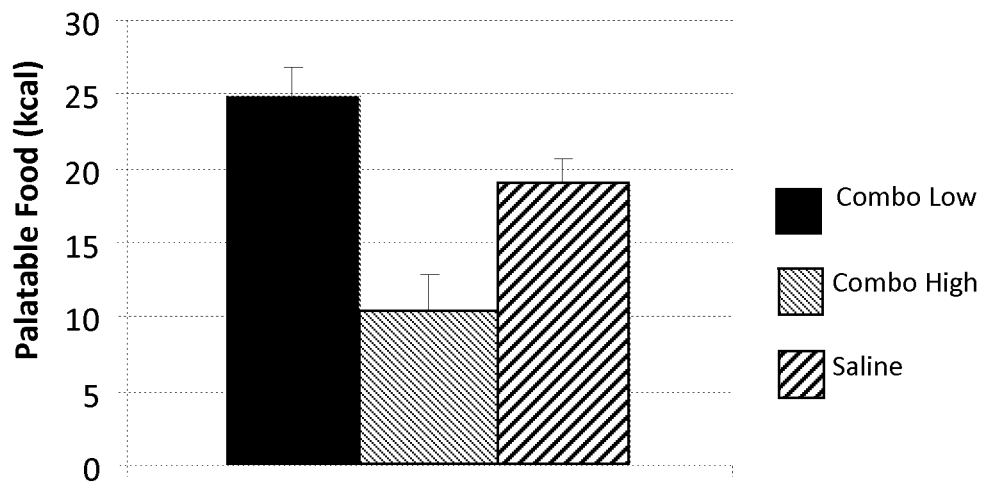
Figure 5A:
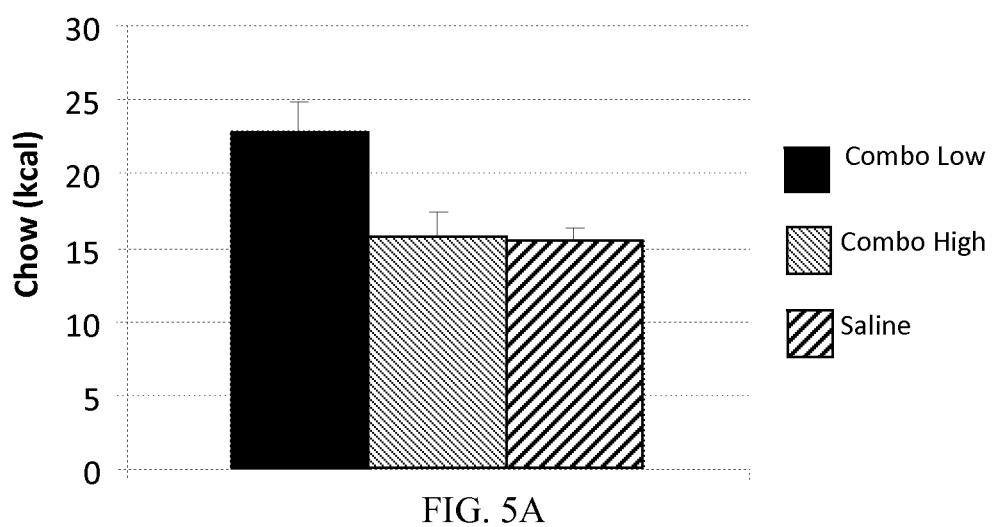
FIGS. 5A-5C. The effect of baclofen/naltrexone on suppressing palatable food intake is specific to palatable food regardless of the group tested. No effects were seen on the intake of plain chow.
Figure 5B:
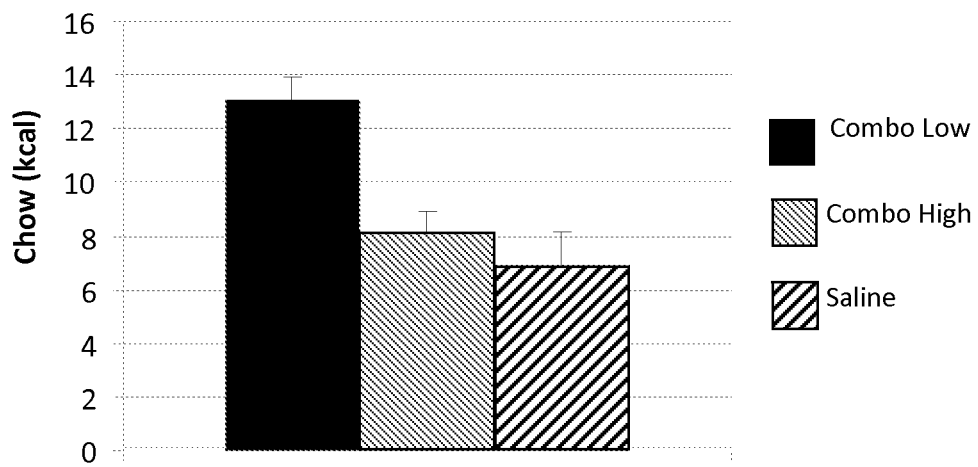
Figure 5C:
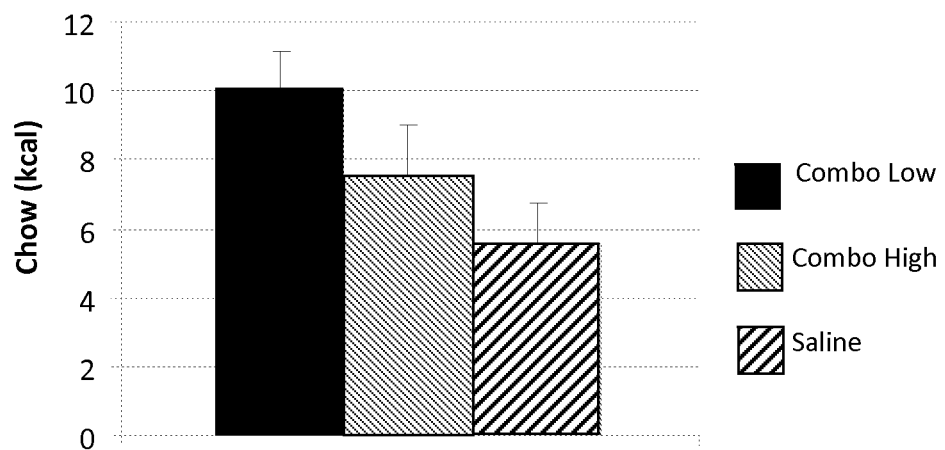

Drugs (2 doses/drug)
Baclofen (at 1.0 and 1.8 mg/kg, administered i.p.)
Naltrexone (at 0.1 and 1.0 mg/kg, administered i.p.)
Baclofen+naltrexone (mixed low and mixed high)
Saline
Groups (n=10/group)
1. Binge Sugar (10% sucrose solution, w/v)
2. Binge Fat (35% oil emulsion, w/v)
3. Binge Sugar/Fat (10% sucrose, 35% oil emulsion, w/v)
Procedure Groups of animals (rats) were maintained on their diets for 3 weeks to establish stable binge eating behavior. After this period of time, the rats were administered three days of daily i.p. injections of saline (to acclimate to the injection procedure), and sugar/chow intake was measured after the first hour of access and then hourly for the next 3 hours, as well as at the end of the 12-h access period. After this three-day period, rats were given baclofen+naloxone, and measurements taken as described above. Other dosage amounts of baclofen and naloxone were tested, as were the effects of these compounds alone (with measurements being performed as described above). Vehicle injections were performed between the various tests in order to allow for suitable clearance of compounds from the animals. Interestingly, the effect of baclofen/naltrexone on suppressing palatable food intake is specific to palatable food (fatty foods, sweet foods or food choices that were both fatty and sweet, see FIGS. 1-5); no effects were seen on the rats' intake of plain chow. Thus, the treatment appears ideally suited for food addicts, hedonic overeaters and changes food choice but not appetite.

Example 2

Materials and Methods

Male Sprague-Dawley rats, 250-300 g at the onset of the experiment, were obtained from Taconic Farms (Germantown, N.Y., USA). Rats were housed individually on a 12-h reversed light/dark cycle and given 1 wk to acclimate before diet training began.

Diets

The rats were divided into groups (n=10/group) matched for body weight and assigned to one of the following dietary conditions: (1) Binge Sugar, (2) Binge Fat or (3) Binge Sugar-Fat. All rats received palatable diets and standard rodent chow (LabDiet #5001, PMI Nutrition International, Richmond, Ind., USA; 10% fat, 20% protein, 70% carbohydrate, 3.02 kcal/g) for 12 h/day, starting 4 h after the onset of the dark cycle. Water was available ad libitum.

All palatable foods were mixed in the laboratory. The Binge Sugar group had access to a 10% (w/v) sucrose solution (Domino® Granulated Pure Cane Sugar, dissolved in tap water, 0.4 kcal/mL), the Binge Fat group had access to a 35% (w/v) fat emulsion (3.1 kcal/mL) and the Binge Sugar-Fat group had access to a 10% (w/v) sugar solution and 35% (w/v) fat emulsion (3.5 kcal/mL). Both emulsions were made with Wesson® Pure Vegetable Oil in tap water and 0.6% (w/v) Emplex, a commercially available emulsifier (American Ingredients Company, Kansas City, Mo., USA). Palatable food intakes were recorded daily. Chow intake was recorded weekly. Body weights were taken at the beginning and end of the 21-day diet period.

Injection Procedures

After 21 days on these diets, drug testing began. During testing, diet regimens were maintained. Approximately 3.5 h into the dark cycle, animals were weighed and intraperitoneal (i.p.) injections of drug were given (according to the schedule below). 30 min later (4 h into the dark cycle) palatable food and chow were made available to the rats. For the first 3 days, rats were acclimated to handling and daily vehicle injections (0.9% saline, Hospira, Lake Forest, Ill., USA, i.p. 1 mL/kg). For days 4-16 of drug testing, either vehicle or drug was alternatively administered, starting with drug on day 4. Drug injections included combinations of R-baclofen (Tocris, Ellisville, Mo., USA) and naltrexone hydrochloride (Sigma, St. Louis, Mo., USA): 0.1 mg/kg naltrexone and 1.0 mg/kg baclofen, or 1.0 mg/kg naltrexone and 1.8 mg/kg baclofen, or either drug was tested alone: 0.1 and 1.0 mg/kg naltrexone, or 1.0 and 1.8 mg/kg baclofen. Intake of palatable food and chow was measured hourly after injection for 4 h and again at the end of the 12-h access period.

Analysis and Statistics

Palatable food and standard chow intakes following saline injections between days 4-16 were averaged. All data were analyzed using one-way ANOVAs with post hoc Multiple Comparisons, when appropriate. In Tables 4-7, values having the same letter superscript are statistically different from one another.

Results

At the beginning of the study, the groups were weight-matched [$F(2,29) \leq 0.001$, 6 p=n.s.; 280.0±3.6 g (Binge Sugar), 280.1±3.4 g (Binge Fat), 280.0±3.6 g (Binge Sugar-Fat)]. There was still no difference in body weight among groups after 21 days on their respective diets [$F(2,29)=0.39$, p=n.s.; 387.2±7.2 g (Binge Sugar), 396.7±5.7 g (Binge Fat), 393.83±10.0 g (Binge Sugar-Fat)], or at the completion of injections [$F(2,29)=1.68$, p=n.s.; 419.9±9.3 g (Binge Sugar), 442.4±6.5 g (Binge Fat), 438.3±11.2 g (Binge Sugar-Fat)].

Effects of Naltrexone, Baclofen or the Combination on Palatable Food Intake

Table 4 shows a summary of palatable food intake in response to the drugs tested as a percent of each groups' saline injections. Naltrexone significantly decreased 1 h ($F(2,29)=3.66$, $p<0.05$, Table 5) and 12-h intake in the Binge Sugar group ($F(2,29)=5.94$, $p<0.01$), with the greatest suppression of intake seen following the higher dose ($p<0.05$). Similar to previous reports (Berner, 2009 #597; Corwin, 2009 #607), there was no effect of baclofen on sugar intake at 1 h ($F(2, 29)=0.79$, p=n.s.) or at 12 h ($F(2,29)=0.13$, p=n.s.). The combination of naltrexone and baclofen decreased sugar intake at 1 h ($F(2,29)=4.067$, $p<0.05$), with the strongest suppression seen at the high-dose combination ($p<0.05$). However, this effect was not apparent at 12 h ($F(2,29)=0.28$, p=n.s.).

For the Binge Fat group, there was no significant effect of naltrexone at 1 h ($F(2,29)=2.55$, p=n.s.) or 12 h ($F(2,29)=0.96$, p=n.s.). Baclofen decreased fat intake at 1 h ($F(2,29)=6.85$, $p<0.01$) and 12 h ($F(2,29)=8.15$, $p<0.01$), with the strongest suppression seen following the higher dose ($p<0.01$). The combination of naltrexone and baclofen also decreased fat intake at 1 h ($F(2,29)=12.11$, $p<0.0001$) and 12 h 7 ($F(2,29)=8.41$, $p<0.01$), again with the strongest suppression seen following the high-dose combination ($p<0.01$).

In terms of the sugar-fat combination, naltrexone had no effect on palatable food intake at 1 h ($F(2,29)=1.84$, p=n.s.) or 12 h ($F(2,29)=1.27$, p=n.s.). Baclofen significantly decreased intake at 1 h ($F(2,29)=9.69$, $p<0.01$) at both doses tested ($p<0.01$). At 12 h, baclofen suppressed intake ($F(2,29)=4.25$, $p<0.05$), with the strongest effect seen following the higher dose ($p<0.05$). Lastly, there was an effect of the naltrexone and baclofen combination on sugar-fat intake at 1 h ($F(2,29)=13.29$, $p<0.0001$), with the strongest suppression seen at the higher dose ($p<0.01$), but no effect was observed at 12 h ($F(2,29)=0.82$, p=n.s.).

Effects of Naltrexone, Baclofen or the Combination on Standard Chow Intake

There was no effect of naltrexone ($F(2,29)=3.31$, p=n.s.; Table 6) or baclofen ($F(2,29)=1.07$, $p>0.05$) on standard chow intake in the Sugar group at 1 h. However, at 12 h, naltrexone ($F(2,29)=6.18$, $p<0.01$) and baclofen ($F(2,28)=4.56$, $p<0.05$) both stimulated chow intake. The combination of naltrexone and baclofen had a significant effect on standard chow intake in the Sugar group at 1 h ($F(2,29)=5.34$, $p<0.05$), with the high dose reducing intake compared to the low dose ($p<0.01$). At 12 h ($F(2,28)=9.32$, $p<0.01$), the combination stimulated intake of standard rodent chow at both drug doses ($p<0.01$, for each) compared to saline.

There was no effect of naltrexone or baclofen alone on standard chow intake in the Fat group at 1 h (naltrexone: $F(2,29)=2.01$, p=n.s.; baclofen $F(2,29)=0.44$, $p>0.05$) or 12 h (naltrexone: $F(2,29)=0.28$, p=n.s.; baclofen: $F(2,29)=0.27$, $p>0.05$; Table 7). There was, however, an effect of the combination of naltrexone and baclofen 1 h ($F(2,29)=10.92$, $p<0.0001$), with less chow intake at the high dose compared to the other two groups (saline: $p<0.05$ and low dose: $p<0.0001$). This effect did not persist, as no significant effect was seen at 12 h ($F(2,29)=0.47$, p=n.s.).

There was no effect of naltrexone on chow intake in the Binge Sugar-Fat group at 1 h ($F(2,29)=0.65$, p=n.s.) or at 12 h ($F(2,29)=0.85$, p=n.s.). Baclofen had a significant effect at 1 h ($F(2,29)=3.58$, $p<0.05$), with less chow intake at the high dose compared to the low dose ($p<0.05$), but not at 12 h ($F(2,28)=0.05$, p=n.s.). There was no effect of the naltrexone and baclofen combination 1 h ($F(2,29)=1.07$, p=n.s.) or 12 h ($F(2,29)=0.46$, p=n.s.).

Effects of Naltrexone, Baclofen or the Combination on Total Caloric Intake

Naltrexone significantly increased total caloric intake in the Sugar group at 1 h ($F(2,29)=4.53$, $p<0.05$; low dose compared to saline $p<0.05$). However, at 12 h, differences were no longer evident ($F(2,27)=3.15$, p=n.s.). Baclofen had no effect on total caloric intake in the Sugar group at 1 h ($F(2,29)=1.63$, p=n.s.) or 12 h ($F(2,26)=3.22$, p=n.s.). The combination of naltrexone and baclofen, however, did significantly reduce total caloric intake 1 h ($F(2,29)=8.11$, $p<0.01$; high dose ($P<0.01$). An effect was still apparent at 12 h ($F(2,26)=6.52$, $p<0.01$), but this time, caloric intake was increased in rats given both the low ($p<0.01$) and high dose ($p<0.05$) of the drug.

In the Fat group, naltrexone had no effect on total caloric intake at 1 h ($F(2,29)=3.25$, $p=n.s.$) or 12 h ($F(2, 29)=1.13$, $p=n.s.$). Baclofen, however, significantly reduced total caloric intake at 1 h ($F(2,29)=6.73$, $p<0.01$) and 12 h ($F(2,29)=4.96$, $p<0.05$), at the high dose, at each time point ($p<0.05$). Likewise, the combination of naltrexone and baclofen reduced total caloric intake at 1 h ($F(2,29)=22.07$, $p<0.0001$) and 12 h ($F(2,29)=8.02$, $p<0.01$), at the high dose at each time point ($p<0.05$).

In the Sugar-Fat group, naltrexone had no effect on total caloric intake at 1 h ($F(2,29)=2.17$, $p=n.s.$) or 12 h ($F(2,27)=1.16$, $p=n.s.$). Conversely, baclofen reduced total caloric intake in the Sugar-Fat group at 1 h ($F(2,29)=15.02$, $p<0.0001$), at the high dose ($p<0.01$), but this effect was not apparent at 12 h ($F(2,27)=2.435$, $p=n.s.$). Likewise, the combination of naltrexone and baclofen reduced total caloric intake at 1 h ($F(2,29)=13.46$, $p<0.0001$), with less intake at the high dose ($p<0.01$), but this effect was not seen at 12 h ($F(2,27)=0.76$, $p=n.s.$).

TABLE 1

Triple Combination Compound Classes

GABA-B agonists and Mu antagonists and CB-1 antagonists
GABA-B agonists and Mu antagonists and Glycine reuptake inhibitors
GABA-B agonists and Mu antagonists and Dopamine augmenting compounds
GABA-B agonists and Mu antagonists and Nicotine receptor agonists
GABA-B agonists and Mu antagonists and Psychostimulants
GABA-B agonists and Mu antagonists and mGlu2/3 agonists
GABA-B agonists and Mu antagonists and mGlu5 antagonists
GABA-B agonists and Mu antagonists and Glycine-site partial agonists
GABA-B agonists and Mu antagonists and Cystine-glutamate exchangers
GABA-B agonists and Mu antagonists and Cystine-glutamate activators
GABA-B agonists and Mu antagonists and Glutamate transporter inhibitors
GABA-B agonists and Mu antagonists and mGlu5 receptor agonists
GABA-B agonists and Mu antagonists and NMDA receptor co-agonists

TABLE 2

Two Compound Combinations baclofen and naltrexone
baclofen and naloxone
baclofen and nalorphine
baclofen and levallorphan
baclofen and buprenorphine
baclofen and extended release naltrexone
baclofen and 2-methyl-4aalpha-(3-hydroxyphenyl)-1,2,3,4,4a,5,12,12aalpha-octahydro-quinolino(2,3-g)isoquinoline (TAN-67)
baclofen and (+)-4-[(αR)-α-((2S,5R)-4-Allyl-2,5-dimethyl-1-piperazinyl)-3-methoxybenzyl]-N,N-diethylbenzamide TABLE 2-continued Two Compound Combinations (SNC80)
lesogaberan and naltrexone
lesogaberan and naloxone
lesogaberan and nalorphine
lesogaberan and levallorphan
lesogaberan and buprenorphine
lesogaberan and extended release naltrexone
lesogaberan and TAN-67
lesogaberan and SNC80
gabapentin and naltrexone
gabapentin and naloxone
gabapentin and nalorphine
gabapentin and levallorphan
gabapentin and buprenorphine
gabapentin and extended release naltrexone
gabapentin and TAN-67
gabapentin and SNC80
pregabalin and naltrexone
pregabalin and naloxone
pregabalin and nalorphine
pregabalin and levallorphan
pregabalin and buprenorphine
pregabalin and extended release naltrexone
pregabalin and TAN-67
pregabalin and SNC80

TABLE 3

Three Compound Combinations baclofen and naltrexone and rimonabant
baclofen and naloxone and N-(Piperidin-1-yl)-5-(4-iodophenyl)-1-(2,4-dichlorophenyl)-4- methyl-1H-pyrazole-3-carboxamide (AM-251)
baclofen and nalorphine and 2-[methyl-[(3R)-3-phenyl-3-[4-(trifluoromethyl)phenoxy]propyl]amino]acetic acid (org24598)
baclofen and naltrexone and acamprosate
baclofen and naltrexone and buprorion
baclofen and naltrexone and buprorion (extended release)
baclofen and naltrexone and nicotine
baclofen and naltrexone and varenicline
baclofen and naloxone and rimonabant
baclofen and naloxone and am-251
baclofen and naloxone and org24598
baclofen and naloxone and acamprosate
baclofen and naloxone and buprorion
baclofen and naloxone and buprorion (extended release)
baclofen and naloxone and nicotine
baclofen and naloxone and varenicline
baclofen and nalorphine and rimonabant
baclofen and nalorphine and am-251
baclofen and nalorphine and org24598
baclofen and nalorphine and acamprosate
baclofen and nalorphine and buprorion
baclofen and nalorphine and buprorion (extended release)
baclofen and nalorphine and nicotine
baclofen and nalorphine and varenicline
baclofen and levallorphan and rimonabant
baclofen and levallorphan and am-251
baclofen and levallorphan and org24598
baclofen and levallorphan and acamprosate
baclofen and levallorphan and buprorion
baclofen and levallorphan and buprorion (extended release)
baclofen and levallorphan and nicotine
baclofen and levallorphan and varenicline
baclofen and buprenorphine and rimonabant
baclofen and buprenorphine and am-251
baclofen and buprenorphine and org24598
baclofen and buprenorphine and acamprosate
baclofen and buprenorphine and buprorion TABLE 3-continued Three Compound Combinations baclofen and buprenorphine and buprorion (extended release)
baclofen and buprenorphine and nicotine
baclofen and buprenorphine and varenicline
baclofen and extended release naltrexone and rimonabant
baclofen and extended release naltrexone and am-251
baclofen and extended release naltrexone and org24598
baclofen and extended release naltrexone and acamprosate
baclofen and extended release naltrexone and buproprion
baclofen and extended release naltrexone and buproprion (extended release)
baclofen and extended release naltrexone and nicotine
baclofen and extended release naltrexone and varenicline
baclofen and tan-67 and rimonabant
baclofen and tan-67 and am-251
baclofen and tan-67 and org24598
baclofen and tan-67 and acamprosate
baclofen and tan-67 and buproprion
baclofen and tan-67 and buproprion (extended release)
baclofen and tan-67 and nicotine
baclofen and tan-67 and varenicline
baclofen and snc80 and rimonabant
baclofen and snc80 and am-251
baclofen and snc80 and org24598
baclofen and snc80 and acamprosate
baclofen and snc80 and buproprion
baclofen and snc80 and buproprion (extended release)
baclofen and snc80 and nicotine
baclofen and snc80 and varenicline
lesogaberan and naltrexone and rimonabant
lesogaberan and naltrexone and am-251
lesogaberan and naltrexone and org24598
lesogaberan and naltrexone and acamprosate
lesogaberan and naltrexone and buproprion
lesogaberan and naltrexone and buproprion (extended release)
lesogaberan and naltrexone and nicotine
lesogaberan and naltrexone and varenicline
lesogaberan and naloxone and rimonabant
lesogaberan and naloxone and am-251
lesogaberan and naloxone and org24598
lesogaberan and naloxone and acamprosate
lesogaberan and naloxone and buproprion
lesogaberan and naloxone and buproprion (extended release)
lesogaberan and naloxone and nicotine
lesogaberan and naloxone and varenicline
lesogaberan and nalorphine and rimonabant
lesogaberan and nalorphine and am-251
lesogaberan and nalorphine and org24598
lesogaberan and nalorphine and acamprosate
lesogaberan and nalorphine and buproprion
lesogaberan and nalorphine and buproprion (extended release)
lesogaberan and nalorphine and nicotine
lesogaberan and nalorphine and varenicline
lesogaberan and levallorphan and rimonabant
lesogaberan and levallorphan and am-251
lesogaberan and levallorphan and org24598
lesogaberan and levallorphan and acamprosate
lesogaberan and levallorphan and buproprion
lesogaberan and levallorphan and buproprion (extended release)
lesogaberan and levallorphan and nicotine
lesogaberan and levallorphan and varenicline
lesogaberan and buprenorphine and rimonabant
lesogaberan and buprenorphine and am-251
lesogaberan and buprenorphine and org24598
lesogaberan and buprenorphine and acamprosate
lesogaberan and buprenorphine and buproprion
lesogaberan and buprenorphine and buproprion (extended release)
lesogaberan and buprenorphine and nicotine
lesogaberan and buprenorphine and varenicline
lesogaberan and extended release naltrexone and rimonabant
lesogaberan and extended release naltrexone and am-251
lesogaberan and extended release naltrexone and org24598
lesogaberan and extended release naltrexone and acamprosate
lesogaberan and extended release naltrexone and buproprion
lesogaberan and extended release naltrexone and buproprion (extended release)
lesogaberan and extended release naltrexone and nicotine
lesogaberan and extended release naltrexone and varenicline
lesogaberan and tan-67 and rimonabant
lesogaberan and tan-67 and am-251
lesogaberan and tan-67 and org24598
lesogaberan and tan-67 and acamprosate
lesogaberan and tan-67 and buproprion
lesogaberan and tan-67 and buproprion (extended release)
lesogaberan and tan-67 and nicotine
lesogaberan and tan-67 and varenicline
lesogaberan and snc80 and rimonabant
lesogaberan and snc80 and am-251
lesogaberan and snc80 and org24598
lesogaberan and snc80 and acamprosate
lesogaberan and snc80 and buproprion
lesogaberan and snc80 and buproprion (extended release)
lesogaberan and snc80 and nicotine
lesogaberan and snc80 and varenicline
gabapentin and naltrexone and rimonabant
gabapentin and naltrexone and am-251
gabapentin and naltrexone and org24598
gabapentin and naltrexone and acamprosate
gabapentin and naltrexone and buproprion
gabapentin and naltrexone and buproprion (extended release)
gabapentin and naltrexone and nicotine
gabapentin and naltrexone and varenicline
gabapentin and naloxone and rimonabant
gabapentin and naloxone and am-251
gabapentin and naloxone and org24598
gabapentin and naloxone and acamprosate
gabapentin and naloxone and buproprion
gabapentin and naloxone and buproprion (extended release)
gabapentin and naloxone and nicotine
gabapentin and naloxone and varenicline
gabapentin and nalorphine and rimonabant
gabapentin and nalorphine and am-251
gabapentin and nalorphine and org24598
gabapentin and nalorphine and acamprosate
gabapentin and nalorphine and buproprion
gabapentin and nalorphine and buproprion (extended release)
gabapentin and nalorphine and nicotine
gabapentin and nalorphine and varenicline
gabapentin and levallorphan and rimonabant
gabapentin and levallorphan and am-251
gabapentin and levallorphan and org24598
gabapentin and levallorphan and acamprosate
gabapentin and levallorphan and buproprion
gabapentin and levallorphan and buproprion (extended release)
gabapentin and levallorphan and nicotine
gabapentin and levallorphan and varenicline
gabapentin and buprenorphine and rimonabant
gabapentin and buprenorphine and am-251
gabapentin and buprenorphine and org24598
gabapentin and buprenorphine and acamprosate
gabapentin and buprenorphine and buproprion
gabapentin and buprenorphine and buproprion (extended release)
gabapentin and buprenorphine and nicotine
gabapentin and buprenorphine and varenicline
gabapentin and extended release naltrexone and rimonabant
gabapentin and extended release naltrexone and am-251
gabapentin and extended release naltrexone and org24598
gabapentin and extended release naltrexone and acamprosate
gabapentin and extended release naltrexone and buproprion
gabapentin and extended release naltrexone and buproprion (extended release)
gabapentin and extended release naltrexone and nicotine TABLE 3-continued Three Compound Combinations gabapentin and extended release naltrexone and varenicline
gabapentin and tan-67 and rimonabant
gabapentin and tan-67 and am-251
gabapentin and tan-67 and org24598
gabapentin and tan-67 and acamprosate
gabapentin and tan-67 and buproprion
gabapentin and tan-67 and buproprion (extended release)
gabapentin and tan-67 and nicotine
gabapentin and tan-67 and varenicline
gabapentin and snc80 and rimonabant
gabapentin and snc80 and am-251
gabapentin and snc80 and org24598
gabapentin and snc80 and acamprosate
gabapentin and snc80 and buproprion
gabapentin and snc80 and buproprion (extended release)
gabapentin and snc80 and nicotine
gabapentin and snc80 and varenicline
pregabalin and naltrexone and rimonabant
pregabalin and naltrexone and am-251
pregabalin and naltrexone and org24598
pregabalin and naltrexone and acamprosate
pregabalin and naltrexone and buproprion
pregabalin and naltrexone and buproprion (extended release)
ppregabalin and naltrexone and nicotine
pregabalin and naltrexone and varenicline
pregabalin and naloxone and rimonabant
pregabalin and naloxone and am-251
pregabalin and naloxone and org24598
pregabalin and naloxone and acamprosate
pregabalin and naloxone and buproprion
pregabalin and naloxone and buproprion (extended release)
pregabalin and naloxone and nicotine
pregabalin and naloxone and varenicline
pregabalin and nalorphine and rimonabant
pregabalin and nalorphine and am-251
pregabalin and nalorphine and org24598
pregabalin and nalorphine and acamprosate
pregabalin and nalorphine and buproprion
pregabalin and nalorphine and buproprion (extended release)
pregabalin and nalorphine and nicotine
pregabalin and nalorphine and varenicline
pregabalin and levallorphan and rimonabant
pregabalin and levallorphan and am-251
pregabalin and levallorphan and org24598
pregabalin and levallorphan and acamprosate
pregabalin and levallorphan and buproprion
pregabalin and levallorphan and buproprion (extended release)
pregabalin and levallorphan and nicotine
pregabalin and levallorphan and varenicline
pregabalin and buprenorphine and rimonabant
pregabalin and buprenorphine and am-251
pregabalin and buprenorphine and org24598
pregabalin and buprenorphine and acamprosate
pregabalin and buprenorphine and buproprion
pregabalin and buprenorphine and buproprion (extended release)
pregabalin and buprenorphine and nicotine
pregabalin and buprenorphine and varenicline
pregabalin and extended release naltrexone and rimonabant
pregabalin and extended release naltrexone and am-251
pregabalin and extended release naltrexone and org24598
pregabalin and extended release naltrexone and acamprosate
pregabalin and extended release naltrexone and buproprion
pregabalin and extended release naltrexone and buproprion (extended release)
pregabalin and extended release naltrexone and nicotine
pregabalin and extended release naltrexone and varenicline
pregabalin and tan-67 and rimonabant
pregabalin and tan-67 and am-251
pregabalin and tan-67 and org24598
pregabalin and tan-67 and acamprosate
pregabalin and tan-67 and buproprion
pregabalin and tan-67 and buproprion (extended release)
pregabalin and tan-67 and nicotine
pregabalin and tan-67 and varenicline
pregabalin and snc80 and rimonabant
pregabalin and snc80 and am-251
pregabalin and snc80 and org24598
pregabalin and snc80 and acamprosate
pregabalin and snc80 and buproprion
pregabalin and snc80 and buproprion (extended release)
pregabalin and snc80 and nicotine
pregabalin and snc80 and varenicline
baclofen and naltrexone and phentermine
baclofen and naltrexone and dexmethylphenidate
baclofen and naltrexone and dextroamphetamine
baclofen and naltrexone and dexedrine
baclofen and naltrexone and Adderall
baclofen and naltrexone and methylphenidate
baclofen and naltrexone and modafanil
baclofen and naltrexone and lisdexamfetamine
baclofen and naloxone and phentermine
baclofen and naloxone and dexmethylphenidate
baclofen and naloxone and dextroamphetamine
baclofen and naloxone and dexedrine
baclofen and naloxone and Adderall
baclofen and naloxone and methylphenidate
baclofen and naloxone and modafanil
baclofen and naloxone and lisdexamfetamine
baclofen and nalorphine and phentermine
baclofen and nalorphine and dexmethylphenidate
baclofen and nalorphine and dextroamphetamine
baclofen and nalorphine and dexedrine
baclofen and nalorphine and Adderall
baclofen and nalorphine and methylphenidate
baclofen and nalorphine and modafanil
baclofen and nalorphine and lisdexamfetamine
baclofen and levallorphan and phentermine
baclofen and levallorphan and dexmethylphenidate
baclofen and levallorphan and dextroamphetamine
baclofen and levallorphan and dexedrine
baclofen and levallorphan and Adderall
baclofen and levallorphan and methylphenidate
baclofen and levallorphan and modafanil
baclofen and levallorphan and lisdexamfetamine
baclofen and buprenorphine and phentermine
baclofen and buprenorphine and dexmethylphenidate
baclofen and buprenorphine and dextroamphetamine
baclofen and buprenorphine and dexedrine
baclofen and buprenorphine and Adderall
baclofen and buprenorphine and methylphenidate
baclofen and buprenorphine and modafanil
baclofen and buprenorphine and lisdexamfetamine
baclofen and extended release naltrexone and phentermine
baclofen and extended release naltrexone and dexmethylphenidate
baclofen and extended release naltrexone and dextroamphetamine
baclofen and extended release naltrexone and dexedrine
baclofen and extended release naltrexone and Adderall
baclofen and extended release naltrexone and methylphenidate
baclofen and extended release naltrexone and modafanil
baclofen and extended release naltrexone and lisdexamfetamine
baclofen and tan-67 and phentermine
baclofen and tan-67 and dexmethylphenidate
baclofen and tan-67 and dextroamphetamine
baclofen and tan-67 and dexedrine
baclofen and tan-67 and Adderall
baclofen and tan-67 and methylphenidate
baclofen and tan-67 and modafanil
baclofen and tan-67 and lisdexamfetamine
baclofen and snc80 and phentermine
baclofen and snc80 and dexmethylphenidate
baclofen and snc80 and dextroamphetamine
baclofen and snc80 and dexedrine
baclofen and snc80 and Adderall
baclofen and snc80 and methylphenidate
baclofen and snc80 and modafanil
baclofen and snc80 and lisdexamfetamine
lesogaberan and naltrexone and phentermine

TABLE 3-continued

Three Compound Combinations lesogaberan and naltrexone and dexmethylphenidate
lesogaberan and naltrexone and dextroamphetamine
lesogaberan and naltrexone and dexedrine
lesogaberan and naltrexone and Adderall
lesogaberan and naltrexone and methylphenidate
lesogaberan and naltrexone and modafanil
lesogaberan and naltrexone and lisdexamfetamine
lesogaberan and naloxone and phentermine
lesogaberan and naloxone and dexmethylphenidate
lesogaberan and naloxone and dextroamphetamine
lesogaberan and naloxone and dexedrine
lesogaberan and naloxone and Adderall
lesogaberan and naloxone and methylphenidate
lesogaberan and naloxone and modafanil
lesogaberan and naloxone and lisdexamfetamine
lesogaberan and nalorphine and phentermine
lesogaberan and nalorphine and dexmethylphenidate
lesogaberan and nalorphine and dextroamphetamine
lesogaberan and nalorphine and dexedrine
lesogaberan and nalorphine and Adderall
lesogaberan and nalorphine and methylphenidate
lesogaberan and nalorphine and modafanil
lesogaberan and nalorphine and lisdexamfetamine
lesogaberan and levallorphan and phentermine
lesogaberan and levallorphan and dexmethylphenidate
lesogaberan and levallorphan and dextroamphetamine
lesogaberan and levallorphan and dexedrine
lesogaberan and levallorphan and Adderall
lesogaberan and levallorphan and methylphenidate
lesogaberan and levallorphan and modafanil
lesogaberan and levallorphan and lisdexamfetamine
lesogaberan and buprenorphine and phentermine
lesogaberan and buprenorphine and dexmethylphenidate
lesogaberan and buprenorphine and dextroamphetamine
lesogaberan and buprenorphine and dexedrine
lesogaberan and buprenorphine and Adderall
lesogaberan and buprenorphine and methylphenidate
lesogaberan and buprenorphine and modafanil
lesogaberan and buprenorphine and lisdexamfetamine
lesogaberan and extended release naltrexone and phentermine
lesogaberan and extended release naltrexone and dexmethylphenidate
lesogaberan and extended release naltrexone and dextroamphetamine
lesogaberan and extended release naltrexone and dexedrine
lesogaberan and extended release naltrexone and Adderall
lesogaberan and extended release naltrexone and methylphenidate
lesogaberan and extended release naltrexone and modafanil
lesogaberan and extended release naltrexone and lisdexamfetamine
lesogaberan and tan-67 and phentermine
lesogaberan and tan-67 and dexmethylphenidate
lesogaberan and tan-67 and dextroamphetamine
lesogaberan and tan-67 and dexedrine
lesogaberan and tan-67 and Adderall
lesogaberan and tan-67 and methylphenidate
lesogaberan and tan-67 and modafanil
lesogaberan and tan-67 and lisdexamfetamine
lesogaberan and snc80 and phentermine
lesogaberan and snc80 and dexmethylphenidate
lesogaberan and snc80 and dextroamphetamine
lesogaberan and snc80 and dexedrine
lesogaberan and snc80 and Adderall
lesogaberan and snc80 and methylphenidate
lesogaberan and snc80 and modafanil
lesogaberan and snc80 and lisdexamfetamine
gabapentin and naltrexone and phentermine
gabapentin and naltrexone and dexmethylphenidate
gabapentin and naltrexone and dextroamphetamine
gabapentin and naltrexone and dexedrine
gabapentin and naltrexone and Adderall
gabapentin and naltrexone and methylphenidate
gabapentin and naltrexone and modafanil
gabapentin and naltrexone and lisdexamfetamine
gabapentin and naloxone and phentermine
gabapentin and naloxone and dexmethylphenidate
gabapentin and naloxone and dextroamphetamine
gabapentin and naloxone and dexedrine
gabapentin and naloxone and Adderall
gabapentin and naloxone and methylphenidate
gabapentin and naloxone and modafanil
gabapentin and naloxone and lisdexamfetamine
gabapentin and nalorphine and phentermine
gabapentin and nalorphine and dexmethylphenidate
gabapentin and nalorphine and dextroamphetamine
gabapentin and nalorphine and dexedrine
gabapentin and nalorphine and Adderall
gabapentin and nalorphine and methylphenidate
gabapentin and nalorphine and modafanil
gabapentin and nalorphine and lisdexamfetamine
gabapentin and levallorphan and phentermine
gabapentin and levallorphan and dexmethylphenidate
gabapentin and levallorphan and dextroamphetamine
gabapentin and levallorphan and dexedrine
gabapentin and levallorphan and Adderall
gabapentin and levallorphan and methylphenidate
gabapentin and levallorphan and modafanil
gabapentin and levallorphan and lisdexamfetamine
gabapentin and buprenorphine and phentermine
gabapentin and buprenorphine and dexmethylphenidate
gabapentin and buprenorphine and dextroamphetamine
gabapentin and buprenorphine and dexedrine
gabapentin and buprenorphine and Adderall
gabapentin and buprenorphine and methylphenidate
gabapentin and buprenorphine and modafanil
gabapentin and buprenorphine and lisdexamfetamine
gabapentin and extended release naltrexone and phentermine
gabapentin and extended release naltrexone and dexmethylphenidate
gabapentin and extended release naltrexone and dextroamphetamine
gabapentin and extended release naltrexone and dexedrine
gabapentin and extended release naltrexone and Adderall
gabapentin and extended release naltrexone and methylphenidate
gabapentin and extended release naltrexone and modafanil
gabapentin and extended release naltrexone and lisdexamfetamine
gabapentin and tan-67 and phentermine
gabapentin and tan-67 and dexmethylphenidate
gabapentin and tan-67 and dextroamphetamine
gabapentin and tan-67 and dexedrine
gabapentin and tan-67 and Adderall
gabapentin and tan-67 and methylphenidate
gabapentin and tan-67 and modafanil
gabapentin and tan-67 and lisdexamfetamine
gabapentin and snc80 and phentermine
gabapentin and snc80 and dexmethylphenidate
gabapentin and snc80 and dextroamphetamine
gabapentin and snc80 and dexedrine
gabapentin and snc80 and Adderall
gabapentin and snc80 and methylphenidate
gabapentin and snc80 and modafanil
gabapentin and snc80 and lisdexamfetamine
pregabalin and naltrexone and phentermine
pregabalin and naltrexone and dexmethylphenidate
pregabalin and naltrexone and dextroamphetamine
pregabalin and naltrexone and dexedrine
pregabalin and naltrexone and Adderall
pregabalin and naltrexone and methylphenidate
pregabalin and naltrexone and modafanil
pregabalin and naltrexone and lisdexamfetamine
pregabalin and naloxone and phentermine
pregabalin and naloxone and dexmethylphenidate
pregabalin and naloxone and dextroamphetamine
pregabalin and naloxone and dexedrine
pregabalin and naloxone and Adderall
pregabalin and naloxone and methylphenidate
pregabalin and naloxone and modafanil
pregabalin and naloxone and lisdexamfetamine
pregabalin and nalorphine and phentermine
pregabalin and nalorphine and dexmethylphenidate
pregabalin and nalorphine and dextroamphetamine
pregabalin and nalorphine and dexedrine
pregabalin and nalorphine and Adderall
pregabalin and nalorphine and methylphenidate
pregabalin and nalorphine and modafanil
pregabalin and nalorphine and lisdexamfetamine
pregabalin and levallorphan and phentermine
pregabalin and levallorphan and dexmethylphenidate
pregabalin and levallorphan and dextroamphetamine
pregabalin and levallorphan and dexedrine
pregabalin and levallorphan and Adderall

TABLE 3-continued

Three Compound Combinations pregabalin and levallorphan and methylphenidate
pregabalin and levallorphan and modafanil
pregabalin and levallorphan and lisdexamfetamine
pregabalin and buprenorphine and phentermine
pregabalin and buprenorphine and dexmethylphenidate
pregabalin and buprenorphine and dextroamphetamine
pregabalin and buprenorphine and dexedrine
pregabalin and buprenorphine and Adderall
pregabalin and buprenorphine and methylphenidate
pregabalin and buprenorphine and modafanil
pregabalin and buprenorphine and lisdexamfetamine
pregabalin and extended release naltrexone and phentermine
pregabalin and extended release naltrexone and dexmethylphenidate
pregabalin and extended release naltrexone and dextroamphetamine
pregabalin and extended release naltrexone and dexedrine
pregabalin and extended release naltrexone and Adderall
pregabalin and extended release naltrexone and methylphenidate
pregabalin and extended release naltrexone and modafanil
pregabalin and extended release naltrexone and lisdexamfetamine
pregabalin and tan-67 and phentermine
pregabalin and tan-67 and dexmethylphenidate
pregabalin and tan-67 and dextroamphetamine
pregabalin and tan-67 and dexedrine
pregabalin and tan-67 and Adderall
pregabalin and tan-67 and methylphenidate
pregabalin and tan-67 and modafanil
pregabalin and tan-67 and lisdexamfetamine
pregabalin and snc80 and phentermine
pregabalin and snc80 and dexmethylphenidate
pregabalin and snc80 and dextroamphetamine
pregabalin and snc80 and dexedrine
pregabalin and snc80 and Adderall
pregabalin and snc80 and methylphenidate
pregabalin and snc80 and modafanil
pregabalin and snc80 and lisdexamfetamine
baclofen and naltrexone and n-acetylcysteine
baclofen and naltrexone and d-cycloserine
baclofen and naltrexone and ceftriaxone
baclofen and naloxone and n-acetylcysteine
baclofen and naloxone and d-cycloserine
baclofen and naloxone and ceftriaxone
baclofen and nalorphine and n-acetylcysteine
baclofen and nalorphine and d-cycloserine
baclofen and nalorphine and ceftriaxone
baclofen and levallorphan and n-acetylcysteine
baclofen and levallorphan and d-cycloserine
baclofen and levallorphan and ceftriaxone
baclofen and buprenorphine and n-acetylcysteine
baclofen and buprenorphine and d-cycloserine
baclofen and buprenorphine and ceftriaxone
baclofen and extended release naltrexone and n-acetylcysteine
baclofen and extended release naltrexone and d-cycloserine
baclofen and extended release naltrexone and ceftriaxone
baclofen and tan-67 and n-acetylcysteine
baclofen and tan-67 and d-cycloserine
baclofen and tan-67 and ceftriaxone
baclofen and snc80 and n-acetylcysteine
baclofen and snc80 and d-cycloserine
baclofen and snc80 and ceftriaxone
lesogaberan and naltrexone and n-acetylcysteine
lesogaberan and naltrexone and d-cycloserine
lesogaberan and naltrexone and ceftriaxone
lesogaberan and naloxone and n-acetylcysteine
lesogaberan and naloxone and d-cycloserine
lesogaberan and naloxone and ceftriaxone
lesogaberan and nalorphine and n-acetylcysteine
lesogaberan and nalorphine and d-cycloserine
lesogaberan and nalorphine and ceftriaxone
lesogaberan and levallorphan and n-acetylcysteine
lesogaberan and levallorphan and d-cycloserine
lesogaberan and levallorphan and ceftriaxone
lesogaberan and buprenorphine and n-acetylcysteine
lesogaberan and buprenorphine and d-cycloserine
lesogaberan and buprenorphine and ceftriaxone
lesogaberan and extended release naltrexone and n-acetylcysteine
lesogaberan and extended release naltrexone and d-cycloserine
lesogaberan and extended release naltrexone and ceftriaxone
lesogaberan and tan-67 and n-acetylcysteine
lesogaberan and tan-67 and d-cycloserine
lesogaberan and tan-67 and ceftriaxone
lesogaberan and snc80 and n-acetylcysteine
lesogaberan and snc80 and d-cycloserine
lesogaberan and snc80 and ceftriaxone
gabapentin and naltrexone and n-acetylcysteine
gabapentin and naltrexone and d-cycloserine
gabapentin and naltrexone and ceftriaxone
gabapentin and naloxone and n-acetylcysteine
gabapentin and naloxone and d-cycloserine
gabapentin and naloxone and ceftriaxone
gabapentin and nalorphine and n-acetylcysteine
gabapentin and nalorphine and d-cycloserine
gabapentin and nalorphine and ceftriaxone
gabapentin and levallorphan and n-acetylcysteine
gabapentin and levallorphan and d-cycloserine
gabapentin and levallorphan and ceftriaxone
gabapentin and buprenorphine and n-acetylcysteine
gabapentin and buprenorphine and d-cycloserine
gabapentin and buprenorphine and ceftriaxone
gabapentin and extended release naltrexone and n-acetylcysteine
gabapentin and extended release naltrexone and d-cycloserine
gabapentin and extended release naltrexone and ceftriaxone
gabapentin and tan-67 and n-acetylcysteine
gabapentin and tan-67 and d-cycloserine
gabapentin and tan-67 and ceftriaxone
gabapentin and snc80 and n-acetylcysteine
gabapentin and snc80 and d-cycloserine
gabapentin and snc80 and ceftriaxone
pregabalin and naltrexone and n-acetylcysteine
pregabalin and naltrexone and d-cycloserine
pregabalin and naltrexone and ceftriaxone
pregabalin and naloxone and n-acetylcysteine
pregabalin and naloxone and d-cycloserine
pregabalin and naloxone and ceftriaxone
pregabalin and nalorphine and n-acetylcysteine
pregabalin and nalorphine and d-cycloserine
pregabalin and nalorphine and ceftriaxone
pregabalin and levallorphan and n-acetylcysteine
pregabalin and levallorphan and d-cycloserine
pregabalin and levallorphan and ceftriaxone
pregabalin and buprenorphine and n-acetylcysteine
pregabalin and buprenorphine and d-cycloserine
pregabalin and buprenorphine and ceftriaxone
pregabalin and extended release naltrexone and n-acetylcysteine
pregabalin and extended release naltrexone and d-cycloserine
pregabalin and extended release naltrexone and ceftriaxone
pregabalin and tan-67 and n-acetylcysteine
pregabalin and tan-67 and d-cycloserine
pregabalin and tan-67 and ceftriaxone
pregabalin and snc80 and n-acetylcysteine
pregabalin and snc80 and d-cycloserine
pregabalin and snc80 and ceftriaxone

TABLE 4

Palatable food intake following drug injections as a percent of intake after saline injections

| Group | Naltrexone | | Baclofen | | Naltrexone-Baclofen | |
|---|---|---|---|---|---|---|
| | low dose | high dose | low dose | high dose | low dose | high dose |
| 1-H Intake (%) | | | | | | |
| Binge Sugar | 158 | 92 | 131 | 96 | 115 | 51 |
| Binge Fat | 70 | 59 | 106 | 38 | 110 | 26 |
| Binge Sugar-Fat | 74 | 75 | 100 | 37 | 106 | 44 |
| 12-H Intake (%) | | | | | | |
| Binge Sugar | 92 | 85 | 88 | 90 | 85 | 82 |
| Binge Fat | 85 | 91 | 93 | 56 | 83 | 59 |
| Binge Sugar-Fat | 92 | 109 | 85 | 75 | 94 | 89 |

TABLE 5

Palatable food intake following drug injections (Kcals)

| Group | Saline | Naltrexone low dose | Naltrexone high dose | Baclofen low dose | Baclofen high dose | Naltrexone-Baclofen low dose | Naltrexone-Baclofen high dose |
|---|---|---|---|---|---|---|---|
| *1-H Palatable Food Intake (Kcal)* | | | | | | | |
| Binge Sugar | 2.8 ± 0.5 | 4.4 ± 0.7$^a$ | 2.6 ± 0.4$^a$ | 3.6 ± 0.8 | 2.7 ± 0.5 | 3.2 ± 0.6$^b$ | 1.4 ± 0.4$^b$ |
| Binge Fat | 16.8 ± 3.0$^{c,h,i}$ | 11.7 ± 1.9 | 9.9 ± 2.0 | 17.9 ± 2.4$^d$ | 6.5 ± 2.0$^{c,d}$ | 18.5 ± 2.3$^g$ | 4.3 ± 1.4$^{g,h}$ |
| Binge Sugar-Fat | 23.5 ± 2.7$^{k,m}$ | 17.3 ± 1.7 | 17.6 ± 3.5 | 23.5 ± 3.9$^j$ | 8.6 ± 1.6$^{j,k}$ | 24.9 ± 1.9$^n$ | 10.4 ± 2.5$^{m,n}$ |
| *12-H Palatable Food Intake (Kcal)* | | | | | | | |
| Binge Sugar | 12.8 ± 2.3 | 18.7 ± 2.4$^r$ | 10.8 ± 1.8$^r$ | 11.3 ± 2.5 | 11.4 ± 2.4 | 10.8 ± 2.3 | 10.4 ± 2.8 |
| Binge Fat | 58.6 ± 6.3$^{e,i}$ | 49.9 ± 3.6 | 53.3 ± 4.5 | 54.5 ± 4.5$^f$ | 32.6 ± 4.9$^{e,f}$ | 48.7 ± 3.8 | 34.8 ± 3.1$^i$ |
| Binge Sugar-Fat | 76.4 ± 5.8$^p$ | 70.6 ± 3.4 | 83.3 ± 8.1 | 64.9 ± 6.6 | 57.4 ± 4.1$^p$ | 71.8 ± 6.5 | 67.9 ± 4.5 |

TABLE 6

Chow intake following drug injections (Kcals)

| Group | Saline | Naltrexone low dose | Naltrexone high dose | Baclofen low dose | Baclofen high dose | Naltrexone-Baclofen low dose | Naltrexone-Baclofen high dose |
|---|---|---|---|---|---|---|---|
| *1-H Chow Intake (Kcal)* | | | | | | | |
| Binge Sugar | 18.2 ± 1.7 | 25.5 ± 3.2 | 20.1 ± 1.3 | 23.0 ± 1.5 | 19.3 ± 3.4 | 23.0 ± 1.8$^d$ | 15.7 ± 1.7$^d$ |
| Binge Fat | 11.3 ± 1.3$^g$ | 8.5 ± 1.1 | 10.1 ± 1.2 | 12.2 ± 1.7 | 10.6 ± 1.0 | 13.1 ± 0.8$^h$ | 8.1 ± 0.7$^{g,h}$ |
| Binge Sugar-Fat | 8.2 ± 1.4 | 6.6 ± 1.0 | 7.1 ± 0.9 | 11.3 ± 1.7$^i$ | 6.3 ± 1.0$^i$ | 10.1 ± 1.1 | 7.5 ± 1.6 |
| *12-H Chow Intake (Kcal)* | | | | | | | |
| Binge Sugar | 58.5 ± 2.7$^{a,b,c,e,f}$ | 73.7 ± 5.1$^a$ | 78.6 ± 4.7$^b$ | 73.5 ± 4.5$^c$ | 62.5 ± 3.8 | 77.0 ± 3.2$^e$ | 75.4 ± 4.5$^f$ |
| Binge Fat | 38.0 ± 3.4 | 34.1 ± 4.3 | 37.0 ± 3.4 | 34.1 ± 3.3 | 35.0 ± 5.0 | 35.1 ± 3.8 | 33.3 ± 3.3 |
| Binge Sugar-Fat | 23.6 ± 2.5 | 26.4 ± 1.9 | 27.4 ± 2.6 | 24.6 ± 2.2 | 24.1 ± 3.1 | 26.3 ± 2.2 | 24.8 ± 1.9 |

TABLE 7

Total caloric intake following drug injections (Kcals)

| Group | Saline | Naltrexone low dose | Naltrexone high dose | Baclofen low dose | Baclofen high dose | Naltrexone-Baclofen low dose | Naltrexone-Baclofen high dose |
|---|---|---|---|---|---|---|---|
| *1-H Total Caloric Intake (Kcal)* | | | | | | | |
| Binge Sugar | 20.9 ± 2.2$^a$ | 29.9 ± 3.9$^a$ | 22.6 ± 1.7 | 26.7 ± 2.3 | 21.9 ± 4.4 | 26.2 ± 2.4$^b$ | 17.1 ± 2.1$^b$ |
| Binge Fat | 28.2 ± 3.4$^{e,h}$ | 20.2 ± 3.0 | 19.9 ± 3.2 | 30.1 ± 4.1$^f$ | 17.0 ± 3.0$^{e,f}$ | 31.6 ± 3.1$^i$ | 12.4 ± 2.1$^{h,i}$ |
| Binge Sugar-Fat | 31.7 ± 4.1$^{k,n}$ | 23.9 ± 2.7 | 24.8 ± 4.4 | 34.8 ± 5.6$^m$ | 15.0 ± 2.6$^{k,m}$ | 35.0 ± 3.0$^o$ | 17.9 ± 4.0$^{n,o}$ |
| *12-H Total Caloric Intake (Kcal)* | | | | | | | |
| Binge Sugar | 71.3 ± 5.0$^{c,d}$ | 85.4 ± 7.5 | 89.4 ± 6.4 | 84.8 ± 7.0 | 74.0 ± 6.3 | 87.9 ± 5.5$^c$ | 85.9 ± 7.3$^d$ |
| Binge Fat | 96.6 ± 9.6$^{g,j}$ | 84.0 ± 7.9 | 90.3 ± 8.3 | 88.6 ± 7.8 | 67.7 ± 9.9$^g$ | 83.7 ± 7.5 | 68.1 ± 6.4$^j$ |
| Binge Sugar-Fat | 100.0 ± 8.3 | 97.0 ± 5.7 | 110.7 ± 10.7 | 89.5 ± 8.8 | 81.4 ± 7.3 | 98.1 ± 8.7 | 92.7 ± 6.3 |

We claim:

1. A pharmaceutical composition comprising a therapeutically effective amount of baclofen or a pharmaceutically acceptable salt thereof; and naltrexone or a pharmaceutically acceptable salt thereof, wherein the therapeutically effective amount of naltrexone or a pharmaceutically acceptable salt thereof is an amount of about 25 to 100 milligrams and baclofen or a pharmaceutically acceptable salt thereof is an amount between about 15 and about 120 milligrams.

2. The composition of claim 1, wherein said composition further comprises a therapeutically effective amount of extended release bupropion or bupropion or a pharmaceutically acceptable salt thereof.

3. The composition according to claim 2, wherein the composition comprises:

naltrexone, or a pharmaceutically acceptable salt thereof, in an amount of about 25 to 100 milligrams, baclofen, or a pharmaceutically acceptable salt thereof, in an amount between about 15 and about 120 milligrams and bupropion or bupropion extended release, or pharmaceutically acceptable salts thereof in an amount of between 75 milligrams and 450 milligrams.

4. A method for reducing the intake of fatty foods, sugar rich foods, or foods that are both fatty and sugar-rich comprising the administration of a composition according to claim 1 to an individual whose diet includes fatty foods, sugar rich foods, or foods that are both fatty and sugar-rich.

5. The method according to claim 4, wherein said individual is an individual meeting the definition of food addiction, an individual who is obese or overweight, has a binge-eating disorder or an individual that engages in binge eating behavior.

6. The pharmaceutical composition of claim 1, wherein the composition comprises synergistic amounts of baclofen and naltrexone.

7. The pharmaceutical composition of claim 6, wherein the composition further comprises extended release bupropion or bupropion or a pharmaceutically acceptable salt thereof.

* * * * *